(12) United States Patent
Healey et al.

(10) Patent No.: US 8,321,049 B2
(45) Date of Patent: Nov. 27, 2012

(54) FLEXIBLE MANUFACTURING SYSTEMS AND METHODS

(75) Inventors: Patrick John Healey, West Chester, OH (US); James Jay Benner, Morrow, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 622 days.

(21) Appl. No.: 12/544,291

(22) Filed: Aug. 20, 2009

(65) Prior Publication Data

US 2011/0046772 A1    Feb. 24, 2011

(51) Int. Cl.
*G06F 19/00* (2011.01)
*G06F 7/66* (2006.01)
*B65B 19/04* (2006.01)
*B31B 1/14* (2006.01)

(52) U.S. Cl. .......... 700/127; 700/117; 158/176; 53/444; 493/346

(58) Field of Classification Search .................. 700/117; 156/176
See application file for complete search history.

(56) References Cited

U.S. PATENT DOCUMENTS

| | | | |
|---|---|---|---|
| 3,860,003 A | 1/1975 | Buell | |
| 4,472,783 A * | 9/1984 | Johnstone et al. | ............ 700/182 |
| 5,151,092 A | 9/1992 | Buell et al. | |
| 5,383,988 A | 1/1995 | Herrmann et al. | |
| 5,492,591 A | 2/1996 | Herrmann et al. | |
| 5,554,145 A | 9/1996 | Roe et al. | |
| 5,569,234 A | 10/1996 | Buell et al. | |
| 5,580,411 A | 12/1996 | Nease et al. | |
| 5,868,899 A | 2/1999 | Gundersen | |
| 6,004,306 A | 12/1999 | Robles et al. | |
| 6,074,333 A | 6/2000 | Rajala et al. | |
| 6,349,237 B1 * | 2/2002 | Koren et al. | .................... 700/96 |
| 6,574,520 B1 | 6/2003 | Liu et al. | |
| 6,788,987 B2 | 9/2004 | Slechta et al. | |
| 6,990,715 B2 | 1/2006 | Liu et al. | |
| 2002/0148548 A1 | 10/2002 | Murie et al. | |

(Continued)

FOREIGN PATENT DOCUMENTS

DE    40 18 266 A1    12/1991

(Continued)

OTHER PUBLICATIONS

U.S. Appl. No. 12/544,268, filed Aug. 20, 2009, James Jay Benner.

(Continued)

*Primary Examiner* — Paul R Myers
*Assistant Examiner* — Christopher a Daley
(74) *Attorney, Agent, or Firm* — Charles R. Matson

(57) ABSTRACT

A converting line comprises a first unit at a first region of the converting line and a second unit at a second region of the converting line. The first unit is positioned in series with the second unit. The converting line further comprises a third unit at a third region of the converting line and a fourth unit at a fourth region of the converting line. The first, second, third, and fourth units are configured to each perform at least one function. The third unit is positioned in parallel with the first unit, the second unit, or the fourth unit. The converting line further comprises a controller configured to activate at least one of the units based a received product order. The converting line is configured to produce a first product different from a second product during a single run of the converting line.

20 Claims, 7 Drawing Sheets

U.S. PATENT DOCUMENTS

| | | | |
|---|---|---|---|
| 2002/0151422 A1 | 10/2002 | Duhm et al. | |
| 2004/0162536 A1 | 8/2004 | Becker et al. | |
| 2006/0286343 A1 | 12/2006 | Curro et al. | |
| 2007/0197987 A1 | 8/2007 | Tsang et al. | |
| 2007/0213678 A1 | 9/2007 | Thorson et al. | |
| 2010/0078119 A1* | 4/2010 | Yamamoto | 156/176 |
| 2010/0170202 A1* | 7/2010 | Bray et al. | 53/444 |

FOREIGN PATENT DOCUMENTS

| | | |
|---|---|---|
| DE | 10 2006 017379 A1 | 10/2007 |
| EP | 0 589 859 A1 | 3/1994 |
| EP | 1 174 377 A2 | 1/2002 |
| EP | 1188426 B1 | 10/2008 |
| WO | WO 00/38608 A1 | 7/2000 |
| WO | WO 01/56523 A1 | 8/2001 |
| WO | WO 01/56524 A1 | 8/2001 |
| WO | WO 2005/005296 A1 | 1/2005 |

OTHER PUBLICATIONS

U.S. Appl. No. 12/544,302, filed Aug. 20, 2009, Patrick John Healey.
U.S. Appl. No. 12/544,346, filed Aug. 20, 2009, James Jay Benner.
U.S. Appl. No. 12/544,363, filed Aug. 20, 2009, Patrick John Healey.
PCT International Search Report dated Feb. 1, 2011, 9 pages.

* cited by examiner

FLEXIBLE MANUFACTURING SYSTEMS AND METHODS

FIELD OF THE INVENTION

The present disclosure generally relates to flexible manufacturing systems and methods and, more particularly, relates to flexible manufacturing systems and methods configured to produce more than one different product during a single run of the flexible manufacturing system.

BACKGROUND OF THE INVENTION

Disposable and durable products, such as absorbent articles, diapers, adult incontinence articles, personal hygiene products, paper towels, feminine hygiene products, sanitary napkins, bandages, underpants, shirts, shorts, swimsuits, gowns, pants, coats, gloves, scarves, surgical drapes, bibs, blankets, sheets, pillow cases, and mops, for example, may be manufactured on production lines such as converting lines. A converting line utilizes a web-based carrier to which many source materials, whether in a continuous web or discrete pieces, are processed and/or attached to the web-based carrier to create a finished product. The process of changing over a production line from producing a first product to producing a second product can be very costly, time consuming, and inefficient. Therefore, this production line technology should be improved.

SUMMARY OF THE INVENTION

In one non-limiting embodiment, the present disclosure, in part, is directed to a machine for manufacturing at least two different absorbent articles during a single run of a production line. The machine comprises a first unit at a first region of the production line and a second unit at a second region of the production line. The first unit is configured to perform a first function and the second unit is configured to perform a second function. The first unit is positioned in series with the second unit. The machine further comprises a third unit at a third region of the production line and a fourth unit at a fourth region of the production line. The third unit is configured to perform a third function and the fourth unit is configured to perform a fourth function. The fourth unit is positioned in series with the second unit. The third unit is positioned in parallel with the first unit, the second unit, or the fourth unit. The machine further comprises a controller configured to activate at least one of the first unit, the second unit, the third unit, and the fourth unit based on a received order for absorbent articles. The machine is configured to produce a first absorbent article having a first intended use and a second absorbent article having a second intended use during the single run of the production line. The first absorbent article is different than the second absorbent article.

In another non-limiting embodiment, the present disclosure, in part, is directed to a converting line for producing different absorbent articles during a single run of the converting line. The converting line comprises a first unit at a first region of the converting line and a second unit at a second region of the converting line. The first unit is configured to perform at least a first function and the second unit is configured to perform at least a second function. The first unit is positioned in series with the second unit. The converting line further comprises a third unit at a third region of the converting line and a fourth unit at a fourth region of the converting line. The third unit is configured to perform at least a third function and the fourth unit is configured to perform at least a fourth function. The third unit is positioned in parallel with the first unit, the second unit, or the fourth unit. The converting line further comprises a controller configured to activate at least one of the first unit, the second unit, the third unit, and the fourth unit based on one or more received orders for absorbent articles. The converting line is configured to produce a first absorbent article and a second absorbent article during the single run of the converting line. The first absorbent article is different than the second absorbent article.

In yet another non-limiting embodiment, the present disclosure, in part, is directed to a method of producing more than one absorbent article during a single run of a production line. The method comprises providing a plurality of units positioned along the production line where each unit is configured to perform at least one function. The method further comprises assembling a first group of the units in series, assembling a second group of the units in parallel with the first group of the units, and providing a base material to the production line. The method further comprises activating at least one function of at least one of the units in the first group or the second group based on a received order for absorbent articles and inactivating at least one function of at least one of the units in the first group or the second group based on the received order for absorbent articles. The method further comprises providing a first path through the production line for a first portion of the base material to produce a first absorbent article and providing a second path through the production line for a second portion of the base material to produce a second absorbent article. The first absorbent article is different than the second absorbent article.

BRIEF DESCRIPTION OF DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein.

DETAILED DESCRIPTION OF THE INVENTION

Figure 1:
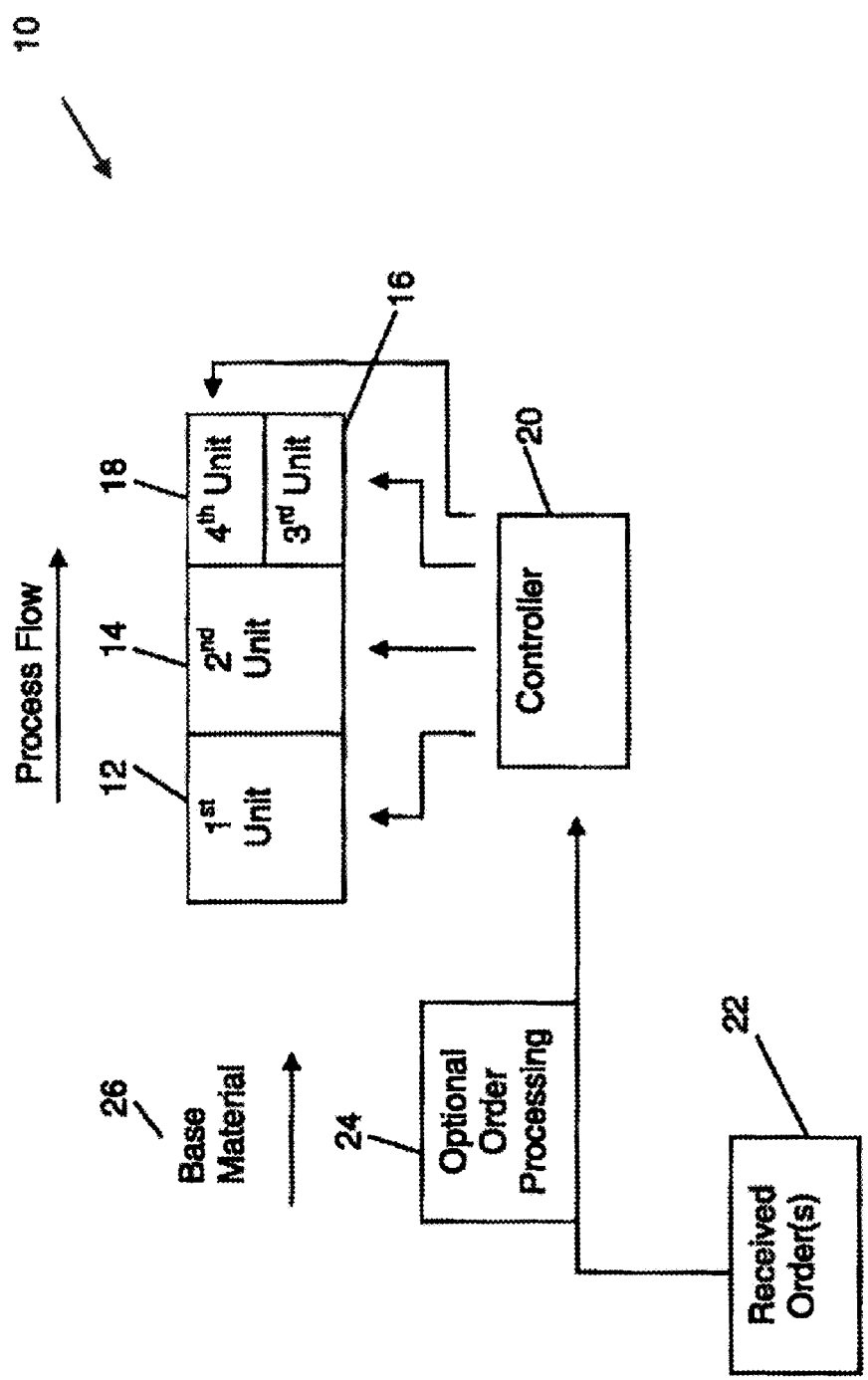
FIG. 1 is a schematic illustration of a production system in accordance with one non-limiting embodiment.

Various non-limiting embodiments of the present disclosure will now be described to provide an overall understanding of the principles of the structure, function, manufacture, and use of the machines and methods disclosed herein. One or more examples of these non-limiting embodiments are illustrated in the accompanying drawings. It will be appreciated that the machines and methods specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

Machines used in production lines, such as converting lines, for example, were initially designed in a unitized fashion, where each individual unit of the machines was driven or actuated primary by a single drive shaft extending along at least most of the length of the production line. The single drive shaft was generally rotated by a single motor to impart motion to the various individual units of the machines when gear boxes, sprockets, timing belts, and/or chains, for example, of the individual units were operably engaged with the single drive shaft. The gear boxes, sprockets, timing belts, and/or chains were used to control the operational speed of each individual unit, for example, while the single drive shaft continuously rotated at a constant speed. These machine designs offered limited flexibility for financially or technically feasible changes beyond what was designed into the original machines prior to construction. Further, these machines were designed for producing a large quantity of a single product (i.e., not two different products) during a single run of the production line.

In other production lines, the machines are driven or actuated by multiple motors positioned in various zones along the production line or by multiple motors where each motor is dedicated to a single function of an individual unit of the machines. Such machines are configured to produce a single product during a single run of the production lines. To changeover from producing a first product to producing a second, different product, components of the machines, such as individual units and/or motors, for example, need to be physically changed out. The machines then need to be restarted and tested to ensure that the second, different product is produced properly, which can waste valuable time, materials, and/or money, for example.

In still other production lines, the machines are comprised of individually functioning units configured to be attached to or operably engaged with other individually functioning units to form the machines. In one example, an individual unit can comprise its own motors or actuators for operating the individual unit, such that the individual unit is essentially self-sufficient, although still working together with other units, when connected with a power source of the production line. An individual unit can be placed into and/or removed from the production line when it is desired to changeover from producing a first product to producing a second, different product. Again, these machines can still only produce an amount of a single product during a single run of the production line without a changeover taking place.

A changeover or an upgrade to a machine can be time consuming and expensive. In fact, product development and implementation of machine upgrades can usually require extensive testing and construction efforts. The machine upgrade may, for example, require the following steps: constructing manual or handmade products incorporating the machine upgrade in order to test the concept and determine consumer acceptance of such a machine upgrade; constructing a machine production unit that may manufacture the machine upgrade and/or the entire product incorporating the machine upgrade in order to determine product and process feasibility; constructing a high speed test stand that may manufacture the machine upgrade in isolation at high speeds in order to test the feasibility of high speed manufacturing; constructing a prototype production line that is able to make complete prototype products at high speeds; reconstructing a high speed production line to implement the process changes necessary for the machine upgrade; and testing and debugging the production line. These efforts may be expensive and time consuming, especially when the reconstruction, testing and debugging steps lead to down time of a high speed production line. Additionally, when a machine upgrade is rolled out on multiple production lines, the cumulative time and money required to implement even a small change in each individual production line may increase dramatically. Often, the time and money required to incorporate the machine upgrades will be prohibitive, and highly desirable machine upgrades may be delayed or even eliminated.

To increase production or product output using the production lines discussed above, generally the production lines were merely run at a higher velocity. Eventually, the production lines, however, may reach a limit of how fast they can be run while still producing a quality product and running efficiently (e.g., without jamming up, without malfunctions, and/or without the need for significant maintenance). Additionally, by merely increasing the velocity of the production lines, the changeover time from producing a first product to producing a second, different product is not reduced. To address these issues, the present disclosure provides machines and methods which can produce more than one different product during a single run of a production line, thereby eliminating costly changeover time while still producing high quality products at a reasonable production line velocity.

The phrases "single run" or "single run of a production line" can mean from a time when the production line begins to produce an amount of a particular product (after a changeover) to a time when the production line ceases producing the amount of the particular product (before another changeover occurs). In general, the phases "single run" or "single run of a production line" do not include a changeover in the production line. The phases "different product" or "different products" can mean two or more products with different intended uses or two or more products with the same intended uses. It will be understood that an amount of each of the different products will be produced during a single run. In one embodiment, the two or more products with different intended uses can be any two of a diaper, a cleaning pad or wipe, a feminine hygiene product, an adult incontinence article, an absorbent pad, a personal hygiene product, a paper towel, a wipe for transferring chemicals to hair and/or skin of humans, dogs, and cats and/or any other suitable products, for example. In one embodiment, the two or more products with the same or similar intended uses can be a first diaper having a first size, pattern, color, weight, shape, absorbency, configuration, fastener system, seams, and/or any other suitable feature and a second diaper having a second size, pattern, color, weight, shape, absorbency, configuration, fastener system, seams, and/or any other suitable feature, for example. In other embodiments, the two or more products with the same intended uses can be a first cleaning pad having a first size, pattern, color, weight, shape, absorbency, configuration and/or any other suitable feature and a second cleaning pad having a second size, pattern, color, weight, shape, absorbency, configuration and/or any other suitable feature, for example In some instances, owing to the lengthy changeover times of the production lines discussed above, the product production schedules of various products have to be projected a few months in advance such that a manufacturer will have enough products in inventory to meet the order demands of customers. In some cases, these production projections are based on historical data regarding customer orders. As such, lead times (i.e., the amount of time between when the product is made and when the customer order is received) can be quite long as a product may only be produced on the production line every few months or every month, for example. A common practice for manufacturers, such that the manufactures are not at a business disadvantage due to this lead time, is to anticipate, speculate, and/or operate from historical data as to what types and quantities of products should be made and to produce the products in advance of a received product order and then place the products in inventory awaiting receipt of an actual customer order. This can cause unproductive inventory. In one example, a manufacturer may produce 50,000 units of a first product during a first run of a production line, while only 5,000 units or no units of the first product have actually been ordered by a customer. During a second run of a second product on the production line, after a changeover, the manufacturer may produce 100,000 units of the second product, even though only 15,000 units of the second product have actually been ordered by customers. One of the disadvantages of this system of production is the large product inventory and consequently the large inventory overhead. This inventory overhead can cost manufacturers a significant amount of money per day just to maintain, store, track, and/or monitor, for example. To minimize such inventory overhead costs, the present disclosure provides machines and methods that can reduce not only product inventory and its associated costs, but also minimize the lead time required to provide an ordered shipment of products to a customer.

In various embodiments, the present disclosure can also provide a production line that can produce different products in an efficient manner and more closely link (in time) received customer orders with the production of the products ordered to significantly reduce significant inventory overhead costs. In one embodiment, the machine can produce more than one different product during a single run of a production line (e.g., a first amount of a first product and a second amount of a second product). The produced products can have the same intended use or a different intended use. Further, the lead time for product orders can be reduced owing to the machine's ability to produce two or more different products during the same run of the production line and/or simultaneously. This ability is a significant advantage over current production systems as manufacturers do not now need to manufacture mass quantities of products and store them in inventory without having any received customer orders.

Of course, manufacturers may still maintain a suitable amount of inventory using the machines and methods of the present disclosure, however, the suitable amount of inventory may be significantly less than the amount of inventory maintained by manufacturers currently. In such an embodiment, received customer orders can be drawn out of the inventory, thereby depleting the suitable amount of the inventory. The suitable amount of the inventory can then be replaced within a short time period using the machines and methods of the present disclosure. In other embodiments, no inventory may be maintained for various products, such as products for which the manufacturer infrequently receives orders and/or for specialty products, for example. When an order is received for these products, the products can then be manufactured to suit the particular order. As a result of the machines and methods of the present disclosure, less product can be manufactured for the purpose of being stored in inventory merely by speculation or historical data, but instead, the products can be manufactured on a more "real time" basis linked to actual customer orders or a financial commitment by a customer.

In one embodiment, the present disclosure can provide machines and methods configured to provide an operator or scheduler of the production line with greater flexibility in scheduling of various products on the production lines. In various embodiments, the operator or scheduler can now decide what products to make immediately before a single run and/or even during a single run. These decisions can be made based on recently received customer orders, for example. This feature can enabled the production line to produce specialty products (e.g., a diaper with a particular pattern, a paper towel with a particular thickness) easily within a single run of the production line without the need for a changeover. This feature also enables the production line to produce a small quantity of these specialty products within a single run of the production line at a significant lower cost than current production line systems due to the fact that no changeover is required as in current production line systems. In one embodiment, during a single run of a production line, 1,000 units of a first product can be produced, then 250 second, specialty products can be produced, and then 4,000 more units of the first product can be produced, for example. This feature can significantly reduce the logical order size (e.g., the amount of a product that is economically feasible to produce and make a profit) to any suitable amount, such as one case, pallet, or shipment of products, for example. The production lines of the present disclosure can accomplish such a result owing, to some extent, to on/off functionality of individual units of the production line and multiple functions that each individual unit can accomplish, as described in further detail below.

In one embodiment, units of a machine of a production line can be activated or inactivated depending on what two different products are being produced. In various embodiments, the units of the machine of the production line or a converting line can be activated, inactivated, and/or can perform a different function or step based on what two different products are being produced. In such an embodiment, when producing a first product, any of the various units can perform a first function or not perform a function at all, and when producing a second product, any of the various units can perform a second function or not perform a function at all, for example. In other embodiments, a first product can have a first path through the production line and a second product can have a second path through the production line. The first path and the second path can be the same or different based on the configuration of the units and the products being produced. In one embodiment, the first path can be different than the second path merely because one of the various units will be inactivated or activated when one of the products is passed thereby on the production line. Although, the machines and methods of the present disclosure are described as producing amounts of more than one product, it will be understood that the machines and methods can also be used to produce an amount of a single product as well.

In one embodiment, the present disclosure can provide machines and methods in which at least two different products can be manufactured during the same run, simultaneously during the same run, or in sequence during the same run, such that the at least two different products can be packaged together for sale. In various embodiments, a first product within a package can have a first intended use and a second product within the package can have a second intended use. The first intended use can be the same as the second intended use. In one example embodiment, a number of daytime diapers or daytime feminine hygiene products can be packaged with a number of nighttime diapers or nighttime feminine hygiene products, respectively, for example. The first intended use can also be different than the second intended use. In such an embodiment, a number of diapers can be packaged with a number of cleaning wipes, for example. Such features of the present disclosure can eliminate or at least reduce the interim step of combining two different products made on more than one production line. This feature can also allow the machines and methods of the present disclosure to produce specialty packages of products. In one example embodiment, a first set of blue diapers can be packaged with a second set of pink diapers for a family having a boy and a girl. These diapers can even be of different sizes, shapes, configurations, orientations, etc.

In one embodiment, the machine can comprise at least two units positioned along and/or forming a production line. In various embodiments, the machine can comprise a plurality of units positioned along and/or forming the production line. The various units can be positioned in parallel and/or in series with each other. In one embodiment, two or more units can be positioned in series with each other, while another unit is positioned in parallel with at least one of the two or more units, for example. The units can each perform a function. In one embodiment, the units can each perform at least one function, and potentially two or more functions depending on the products being produced. In one embodiment, the units can be attached together to form the production line, while still being self-sufficient. Electrical power and any suitable signals can be transferred between the units and the units can be operably linked together such that they can work together and communicate with each other to produce an amount of a product or produce an amount of two or more different products, for example.

In one embodiment, the units can comprise any suitable machine component, which can be configured to be used in a production line. In various embodiments, each of the "units" can comprise more than one machine component or unit. In one embodiment, the units can comprise an applicator device, a dispensing device, a removing device, a printing device, a cutting device, a mixing device, a capping device, a bottling device, a sorting device, a wetting device, a drying device, a heating device, a melting device, a sealing device, a cooling device, a holding device, a testing device, a pressurizing device, a vacuum creating device, a pigment application device, a painting device, a labeling device, a fragrance dispensing device, a stretching device, a compressing device, a perforating device, a scoring device, a sanitizing device, and/or a packaging device, for example. It will be appreciated that any other suitable machine components or units for production lines can also be used and that such units are within the scope of the present disclosure.

The various units discussed above can perform any suitable function to a material on the production line. In one embodiment, at least some of the units can perform more than one function depending on what type of a product is being manufactured on the production line. The functions performed by the units can be any suitable functions that are useful in a production line, such as applying a part, removing a part, attaching a part, affixing a part, molding a part, testing a part, cutting a part, perforating a part, scoring a part, sanitizing a part, compressing a part, stretching a part, holding a part, cooling a part, heating a part, melting a part, sealing a part, wetting a part, drying a part, pressurizing a part, creating a vacuum, applying a cap, bottling a substance or material, sorting a part, labeling a part, applying a fragrance, combining two or more parts, and/or packaging a part, for example. The part can be a portion of the product being produced, a portion configured to be attached to the product, a byproduct of making the product, a base material for making the product, and/or an unfinished version of the product, for example.

It will be recognized that any other suitable production line functions can also be performed by the units and that such functions are within the scope of the present disclosure.

The units and their functions discussed above can be used to produce any suitable products made, packaged, combined, and/or otherwise processed on production lines, such as consumer products, for example. The consumer products can comprise beauty care products, personal care products, baby care products, home care products, food products, health and wellness products, and/or pet products, for example. In other embodiments, the units and their functions discussed above can be used to make, package, combine, and/or otherwise process any suitable products outside of the area of consumer products, such as in the field of appliance manufacturing, for example.

In an exemplary embodiment for the production of absorbent articles, the units can comprise an absorbent material dispensing device, a testing device, a material removing device, a material cutting device, an application device, a pigment application device, a packing device, a packaging device, a material stretching device, a pattern producing device, a tape applying device, an ear applying device, a fastener applying device, a material compressing device, a material sealing device, a material perforating device, a material scoring device, a material heating device, a material cooling device, a material melting device, a dying device, and/or a labeling device, for example. In such an embodiment, the functions of the units can comprise applying an absorbent material to the base material, dispensing a granular material onto the base material, removing a portion of the base material or other material of the product, applying a part to the base material or other material of the product, applying a pattern to the base material or other material of the product, applying a pigment to the base material or other material of the product, packaging finished or substantially finished products, testing finished or substantially finished products, and/or separating one or more finished products or substantially finished products, for example.

In such an exemplary embodiment for making absorbent articles, the absorbent articles can comprise disposable diapers, adult incontinence articles, cleaning pads or wipes, feminine hygiene products, absorbent pads, personal hygiene products, paper towels, napkins, wipes for transferring chemicals to hair and/or skin of humans, dog, and cats and/or any other suitable absorbent article, for example. The absorbent articles produced can also comprise disposable bandages, underpants, shirts, shorts, swimsuits, gowns, pants, coats, gloves, scarves, surgical drapes, bibs, blankets, sheets, pillow cases, and/or mops, for example. It will be appreciated that any other suitable absorbent articles can also be produced.

In various embodiments, the units of the machines can be arranged in any suitable configuration suitable for producing particular products or particular types of products. While various configurations are illustrated in the accompanying drawings, it will be appreciated that the illustrated configurations are merely example configurations and, as such, are not intended to limit the scope of the claims of the present disclosure. In some embodiments, the units can be fixedly attached to each other when assembled to form at least a portion of the production line, while in other embodiments, the units can be removably attached to each other when assembled to form at least a portion of the production line. When the units are removably attached to each other, one unit can easily be changed out for another unit, for example. In one embodiment, a plurality of units can be provided in a machine of a production line. A first group of the plurality of the units can be arranged in series, while a second group of the plurality of the units can be arranged in parallel with at least one of the units in the first group of the plurality of the units.

The phrase "positioned in series" or "in series" can mean positioned in succession along a production line. The phrase "positioned in parallel" or "in parallel" can mean positioned side by side in a branched production line or can mean positioned beside other units in a branched production line.

In one embodiment of the present disclosure, a machine for manufacturing at least two different absorbent articles during a single run of a production line, such as a converting line, for example, is provided. In various embodiments, referring to FIG. 1, a machine 10 can comprise a first unit 12 at a first region of the production line and configured to perform a first function, a second unit 14 at a second region of the production line and configured to perform a second function, a third unit 16 at a third region of the production line and configured to perform a third function, and at least a fourth unit 18 at a fourth region of the production line and configured to perform a fourth function. The first unit 12 can be positioned in series with the second unit 14, while the second unit 14 can be positioned in series with the fourth unit 18 and/or the third unit 16. The third unit 16 can also be positioned in parallel with the first unit 12, the second unit 14, or the fourth unit 18. In one embodiment, the third unit 16 can be positioned in parallel with one or more of the first unit 12, the second unit 14, and the fourth unit 18, for example. The machine 10 can also comprise a controller 20, such as a logic controller or a programmable logic controller, for example. The controller 20 or other controllers discussed herein can be any suitable known controller. In one embodiment, the controller 20 can be in communication with a server 22 configured to receive and track received product order information, with an optional order processor 24 for processing the received orders, and with all or some of the first unit 12, the second unit 14, the third unit 16, and the fourth unit 18. The controller 20 can allow the functions performed by the various units to be activated, inactivated, changed, and/or modified, for example, as will be discussed in further detail below. The machine 10 of the exemplary embodiment of FIG. 1 can be configured to produce a first absorbent article having a first intended use and a second absorbent article having a second intended use during a single run of the production line. The first absorbent article can be the same as or different than the second absorbent article. The first absorbent article can have the same or a different intended use as the second absorbent article. The machine 10 can also be configured to produce non-absorbent products or articles.

In one embodiment, a base material 26, such as a carrier web can be fed into the machine 10 and processed by at least one of the first unit 12, the second unit 14, the third unit 16, and the fourth unit 18. In various embodiments, two or more different products being produced can be determinative of whether one or more or all of the units are activated to perform a function to the base material. In other embodiments, the two or more different products being produced can be determinative of what functions each of the units will perform or not perform. The controller 20 can provide a signal, correlated to the received product order information, to the units indicative of whether to perform a function, what function to perform, and/or whether to inactivate during a particular time interval of a single run of the production line. As such, for example, the first unit 12 can perform a first function to a first portion of the base material 26 and perform a second function to a second portion of the base material 26, a second unit 14 can perform a function to the first and second portions of the base material 26, the third unit 16 can perform a function to the first portion of the base material 26, and the fourth unit 18 can perform a function to the second portion of the base material 26. By placing the third unit 16 in parallel with the fourth unit 18, in this embodiment of the machine 10, the third unit 16 can perform a function to the first portion of the base material 26 at the same time as the fourth unit 18 is performing a function to the second portion of the base material 26.

With respect to other various embodiments and other figures discussed below, it will be understood that when the first unit, the second unit, the third unit, and the fourth unit (and any other units discussed) are discussed, they can be the same as described above (e.g., the first unit configured to perform a first function, the second unit configured to perform a second function). As such, these units will not be described in detail each time they are discussed below for the sake of brevity. The positioning of the first unit, the second unit, the third unit, the fourth unit, and/or other units, however, may be explained with respect to each illustrated embodiment.

Figure 2:
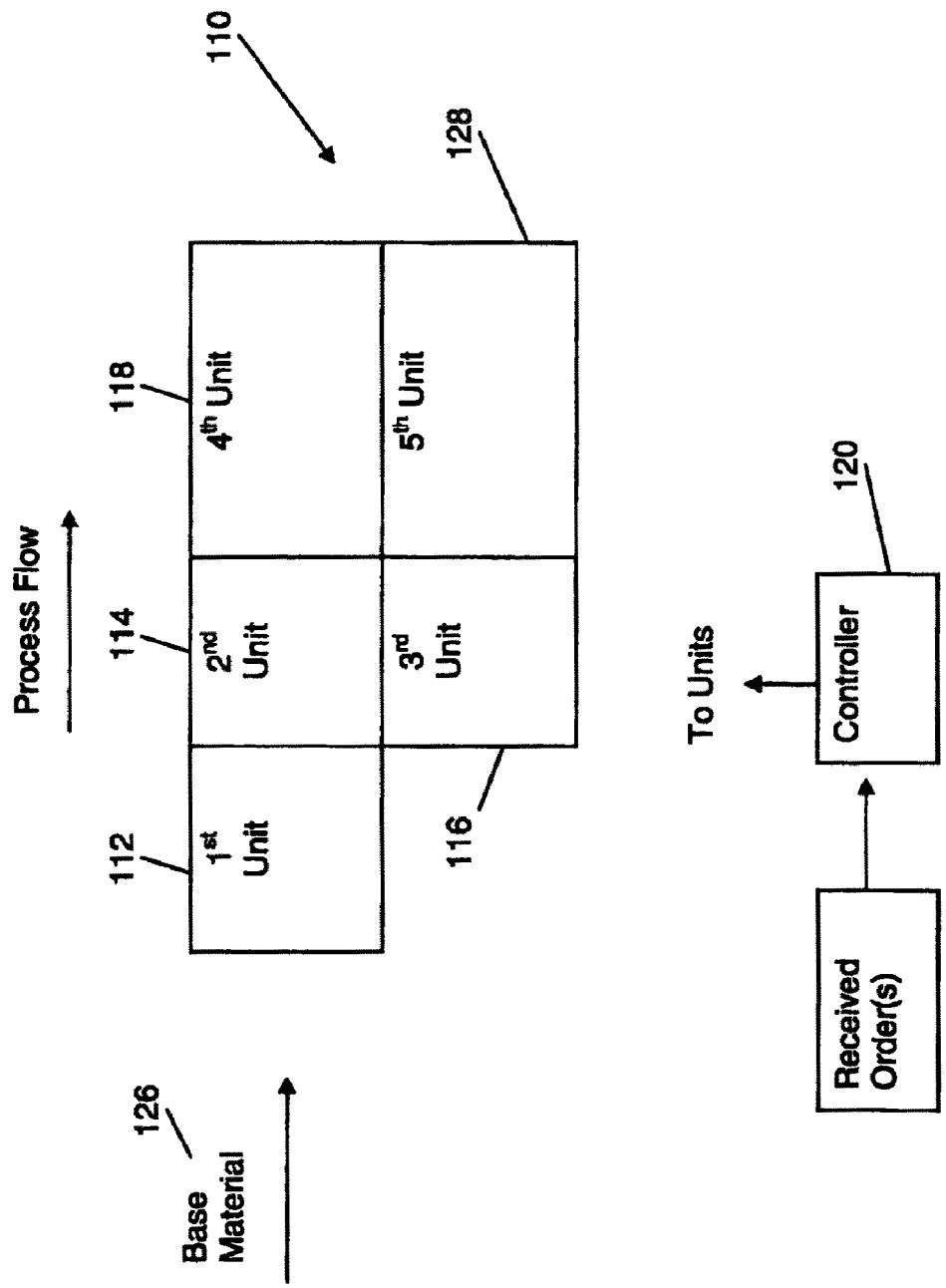
FIG. 2 is another schematic illustration of a production system in accordance with one non-limiting embodiment.

In one embodiment, referring to FIG. 2, another machine 110 for manufacturing at least two different absorbent articles during a single run of a production line, such as a converting line, for example, is provided. In various embodiments, the machine 110 can comprise a first unit 112, a second unit 114, and a fourth unit 118 positioned in series with each other. The machine 110 can also comprise a third unit 116, and a fifth unit 128 at a fifth region of the production line and configured to perform a fifth function. In one embodiment, the third unit 116 can be positioned in parallel with the second unit 114 and the fifth unit 128 can be positioned in parallel with the fourth unit 118. The third unit 116 can also be positioned in series with the fifth unit 128, for example. In such an embodiment, one or both of the second unit 114 and the third unit 116 can be activated to perform a function to the base material 126. Similarly, one or both of the second unit 114 and the third unit 116 can be activated to perform a function to the base material 126. In one embodiment, these various units can be activated or inactivated, or their functions can be varied, by a controller 120 based on a received product order or orders. In one embodiment, the functions of any of the various units of FIG. 2 can be activated or inactivated, and/or their functions varied, based on the received product order or orders. In such an embodiment, the second unit 114 can perform a first function when an order for a first product is received, while the second unit 114 can perform a second and a third function when an order for a second, different product is received, for example. The first and second products can have the same or a different intended use. In one embodiment, the first and second products can be different from each other (e.g., size, shape, weight, color) and/or can be different products (e.g., a diaper and a cleaning pad)

In one embodiment, referring to FIGS. 1 and 2, it will be understood that while the third unit 16 of FIG. 1 is illustrated "in-line" with the production line, it can also extend from the production line as illustrated with respect to the third unit 116 and the fifth unit 128 of FIG. 2. As in FIG. 2, when units of the present disclosure are illustrated extending from being in-line with the linear production line, the production line can actually just have a widened area such that the units are positioned in-line with the production line. In other embodiments, the size of the units can be reduced such that they can fit in-line with the production line (see e.g., the third unit 16 and the fourth unit 18 of FIG. 1). Again referring to FIG. 2, the present disclosure does also contemplate that portions of the base material 126 could, in some applications, travel out of line with the linear flow of the production line to the third unit 116 and the fifth unit 128, and then rejoin the production line further downstream. In still other embodiments, referring to FIG. 2, the base material 126 could flow through the first unit 112 to the third unit 116, and then to the fourth unit 118, for example. The same or similar reasoning will also apply to other various embodiments discussed herein, if applicable.

Figure 3:
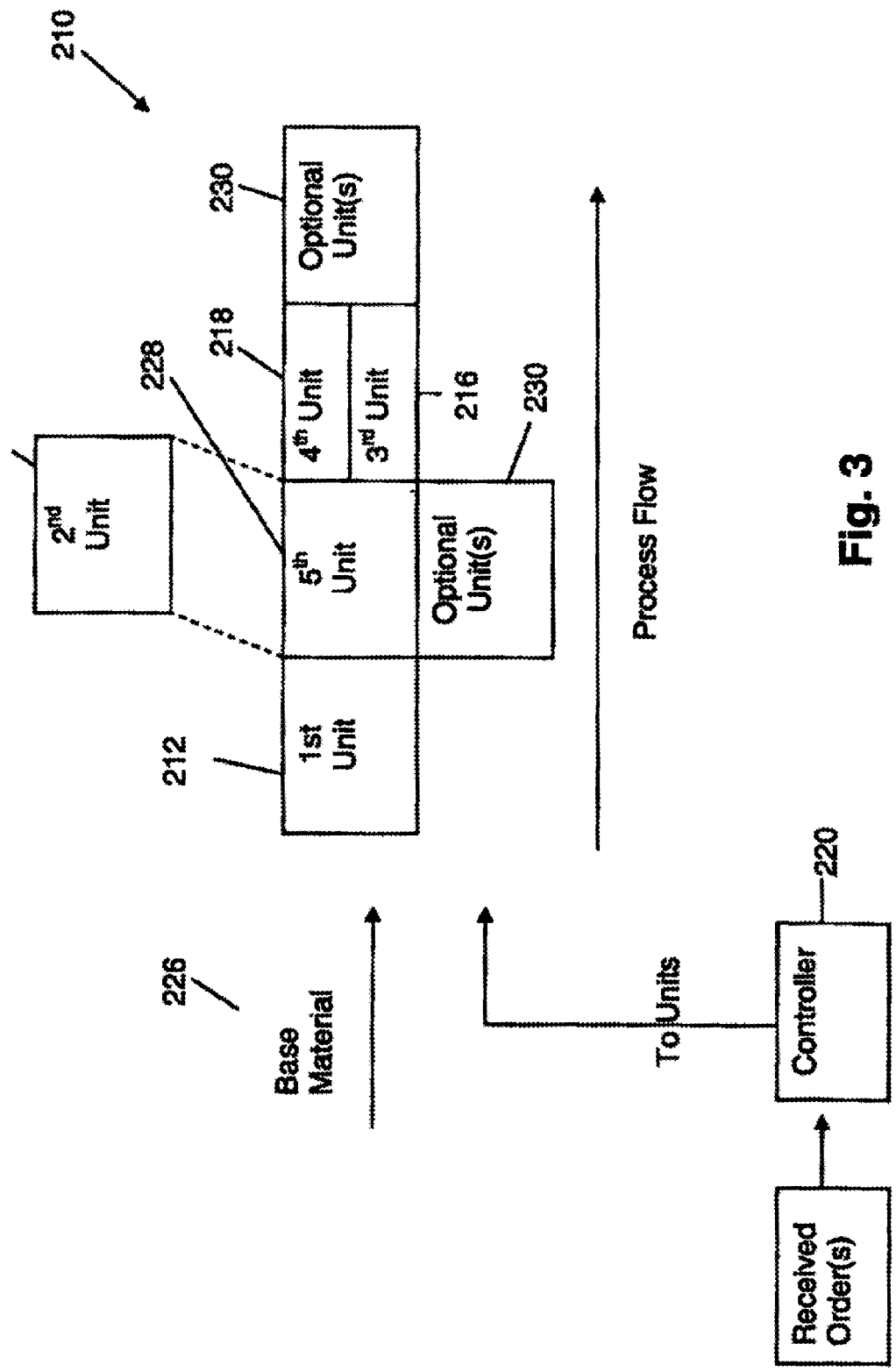
FIG. 3 is yet another schematic illustration of a production system in accordance with one non-limiting embodiment.

In various embodiments, referring to FIG. 3, a machine 210 for manufacturing at least two different absorbent articles during a single run of a production line, such as a converting line, for example, is provided. The machine 210 can comprise a first unit 212, a fifth unit 228, a fourth unit 218, a third unit 216, and one or more optional units 230. The first unit 212, the fifth unit 228, the fourth unit 218 and the third unit 216, and the one or more optional units 230 can be positioned in series with each other, while the fourth unit 218 and the third unit 216 can be positioned in parallel with each other. In such an embodiment, the one or more optional units 230 can be configured to be positioned in parallel with a region of the machine 210 where the fifth unit 228 is located, for example. In one embodiment, the fifth unit 228, for example, can be changed out and a second unit 214 can take the fifth units' place in the production line. Of course, the second unit 214 can comprise more than one unit having more than one function per unit. In one embodiment, the fifth unit 228 can be slid out or moved of the production line on rails (not illustrated), for example, while the second unit 214 can be slid or moved into the production line from the other side of the production line, for example. In other embodiments, any other suitable method of changing out units of a production line can be used. When the second unit 214 is inserted into the production line, it can be ready to be operated after electrical connections are made, thereby significantly reducing changeover times. While not illustrated in other example embodiments of the production line, it will be understood that any of the various units can be changed out with one or more other units and/or optional units, for example, based on a particular production line need.

In one embodiment, referring again to FIG. 3, any or all of the units can activate, inactivate, and/or perform one or more functions based on the instructions they receive from a controller 220, which is configured to receive and transmit instructions corresponding to received product orders to at least some of the units. In various embodiments, the functions of the units can be changed during a single run of the production line, for example, using the controller 220. In one example embodiment of operation, the first unit 212 can apply an absorbent material to a base material 226 being fed into the production line, the fifth unit 228 can apply a top sheet to the absorbent material to at least partially form an absorbent article, and the fourth unit 218 can remove a portion of the absorbent article or add a part to the absorbent article based on the received product order. The third unit 216 can apply a first design, a second design, and/or a third design to the absorbent article again based on the received product order. In one embodiment, the third unit 216 may not apply a design to the absorbent article at all based on the received product order. The one or more optional units 230 positioned in series after the third unit 216 and the fourth unit 218 can perform any of the functions listed herein to the absorbent articles to finish the production or processing of the absorbent articles and/or to package the absorbent articles, for example. Of course, the absorbent articles referenced above are merely example embodiments, and it will be appreciated that the machine 210 can function in a similar fashion when producing other products.

Figure 4:
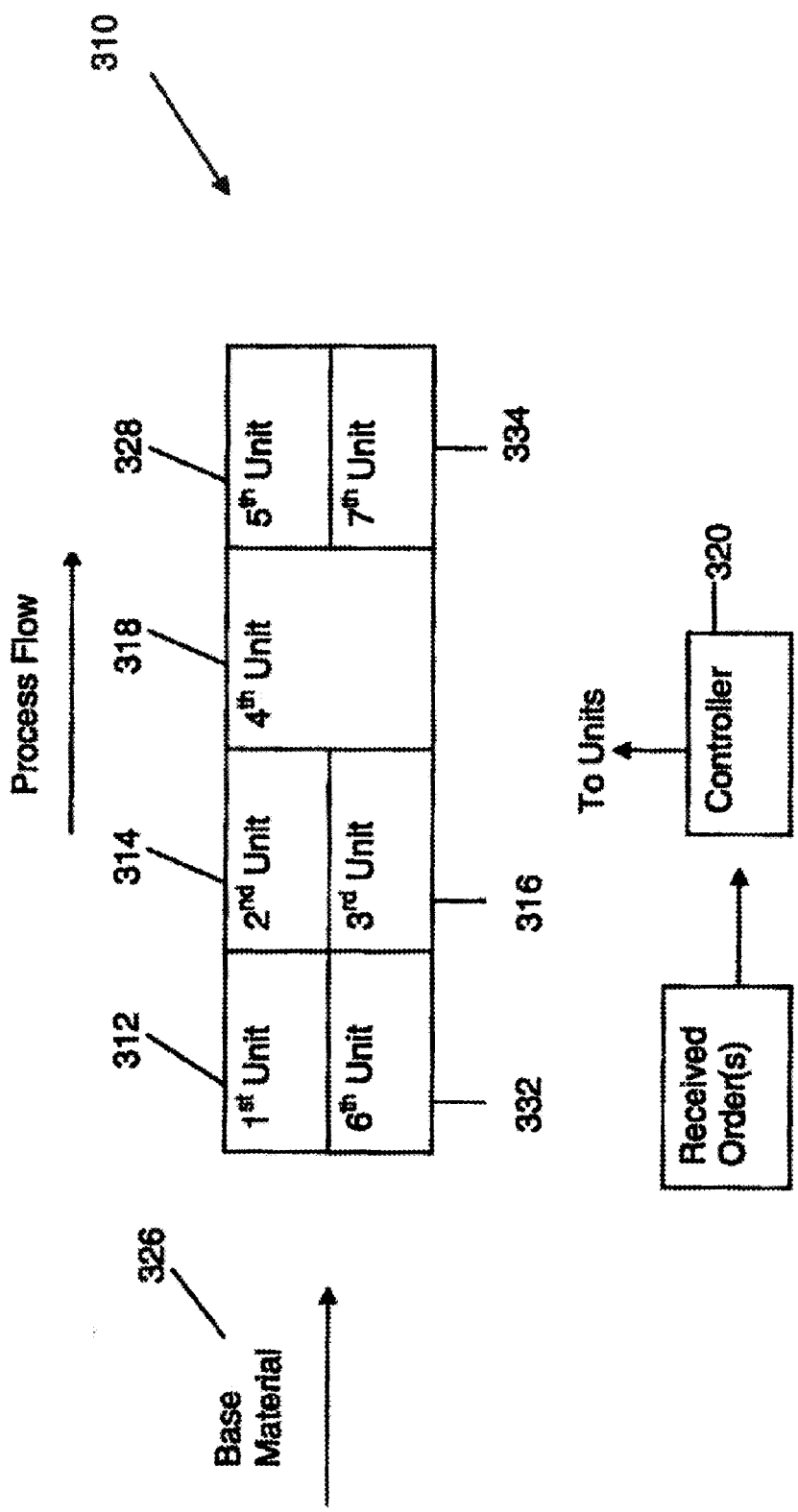
FIG. 4 is still another schematic illustration of a production system in accordance with one non-limiting embodiment.

In one embodiment, referring to FIG. 4, a machine 310 for manufacturing at least two different absorbent articles during a single run of a production line, such as a converting line, for example, is provided. The machine 310 can comprise a sixth unit 332 at a sixth region of the production line and configured to perform a sixth function and a seventh unit 334 at a seventh region of the production line and configured to perform a seventh function. The machine 310 can also comprise a first unit 312, a second unit 314, a third unit 316, a fourth unit 318, and a fifth unit 328. An example configuration, orientation, and/or arrangement of the units of the machine 310 is illustrated in FIG. 4.

Figure 5:
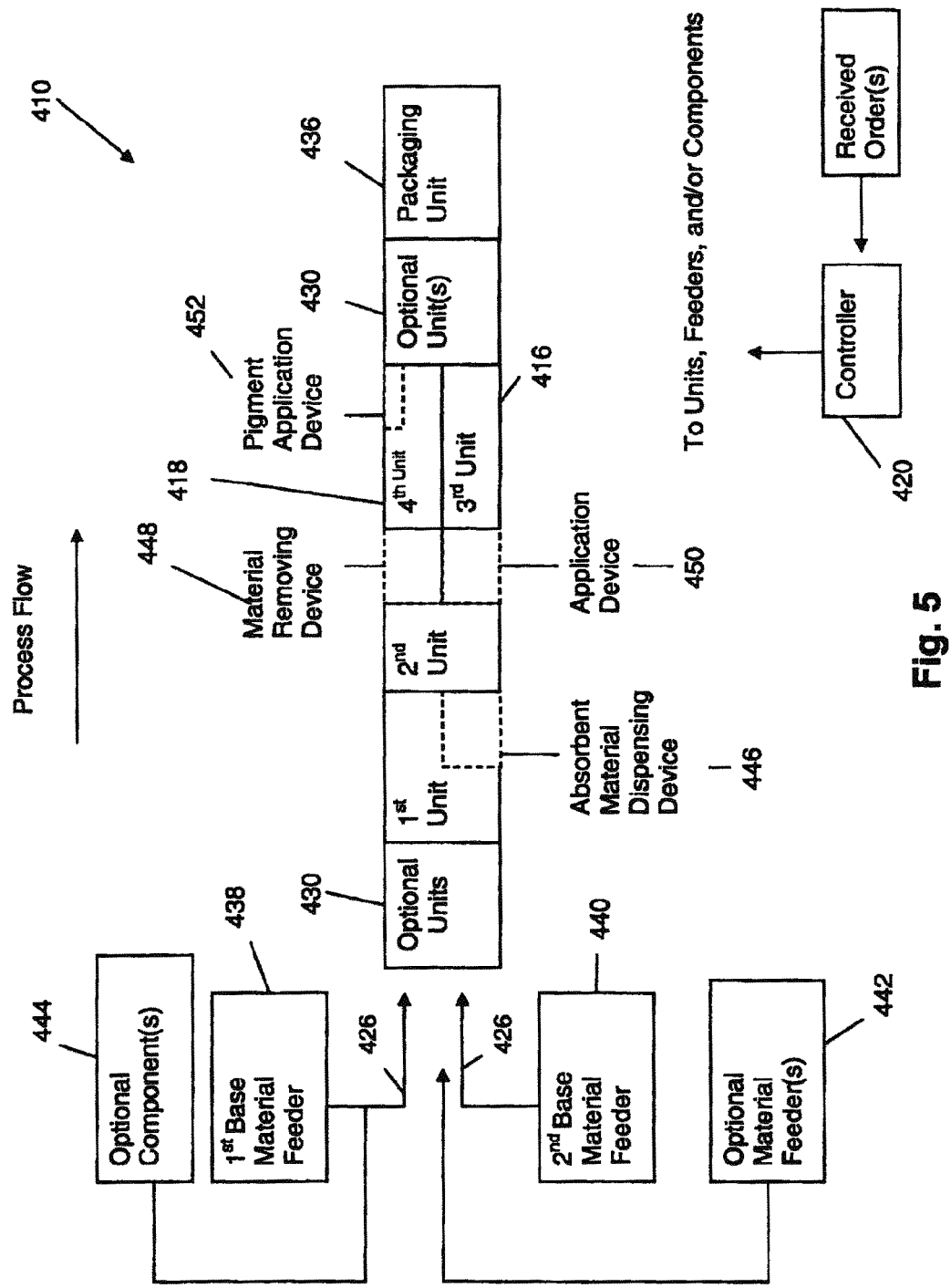
FIG. 5 is still another schematic illustration of a production system illustrating various components used for feeding a base material into a production line in accordance with one non-limiting embodiment.

In one embodiment, referring to FIG. 5, a machine 410 for manufacturing at least two different absorbent articles during a single run of a production line, such as a converting line, for example, is provided. In various embodiments, the machine 410 can comprise a first unit 412, a second unit 414, a third unit 416, a fourth unit 418, one or more optional units 430, a packaging unit 436, a first base material feeder 438, a second base material feeder 440, one or more optional material feeders 442, and other various optional components 444 relating to the base material feed system. The machine 410 can also comprise a controller 420 in communication with the various units, feeders, and/or components. The controller 420 can be configured to receive received order information and then send signals to the various units, feeders, and/or components such that products can be made in accordance with the received order information.

In one embodiment, again referring to FIG. 5, one or more optional units 430, the first unit 412, the second unit 414, the third and fourth units 418 and 416, again one or more optional units 430, and a packaging unit 436 can all be positioned in series. The third unit 416 and the fourth unit 418, however, can be positioned in parallel with each other. The first unit 412 can comprise an absorbent material dispensing device 446 configured to dispense an absorbent material onto a base material 426 being fed into the production line using at least one of the base material feeders 438, 440, and 442 or other material feeders. In one embodiment, the absorbent material dispensing device 446 can be configured to apply a first amount of an absorbent material to a first portion of the base material 426 for formation of a first absorbent article and can be configured to apply a second amount of the absorbent material to a second portion of the base material 426 for formation of a second absorbent article. The second unit 414 can comprise a material removing device 448 and an application device 450. In one embodiment, the material removing device 448 can remove a portion of the base material 426, a portion of the absorbent material, and/or a portion of another material which was applied to the base material 426 by the one or more optional units 430 to form at least an intermediate stage absorbent article or other product. In various embodiments, the material removing device 448 can be configured to remove a first amount of the base material 426 from a first portion of the base material 426 for formation of a first absorbent article and can be configured to remove a second amount of the base material 426 from a second portion of the base material 426 for formation of a second absorbent article. In one embodiment, the application device 450 can be configured to apply a part or piece of material to the base material 426, to the absorbent material, and/or to another material which was applied to the base material 426 by the one or more optional units 430. In an example embodiment, the application device 450 can apply ears, tape, elastic, fasteners, and/or top sheets. In one embodiment, the application device 450 can be configured to apply a first item to a first portion of the base material 426 for formation of a first absorbent article and can be configured to apply a second item to a second portion of the base material 426 for formation of a second absorbent article. The fourth unit 418 can comprise a pigment application device 452. The pigment application device 452 can apply pigments, such as dyes or inks, for example, to the base material 426 or to any other material positioned on or attached to the base material 426. In one embodiment, the pigment application device 452 can apply a first pattern, a second pattern, and at least a third pattern. In one embodiment, the pigment application device 452 can be configured to apply a first amount of a pigment to a first absorbent article in a first pattern and can be configured to apply a second amount of the pigment to a second absorbent article in a second pattern. In other embodiments, the pigment application device 452 may not be actuated and, as such, it will not apply a pattern to products or articles on the production line at all. In various embodiments, the packaging unit 436 can be used to packing products produced on the production line. In one embodiment, the packaging unit 436 can package a first absorbent article or product and a second, different absorbent article or product together, for example.

Figure 7:
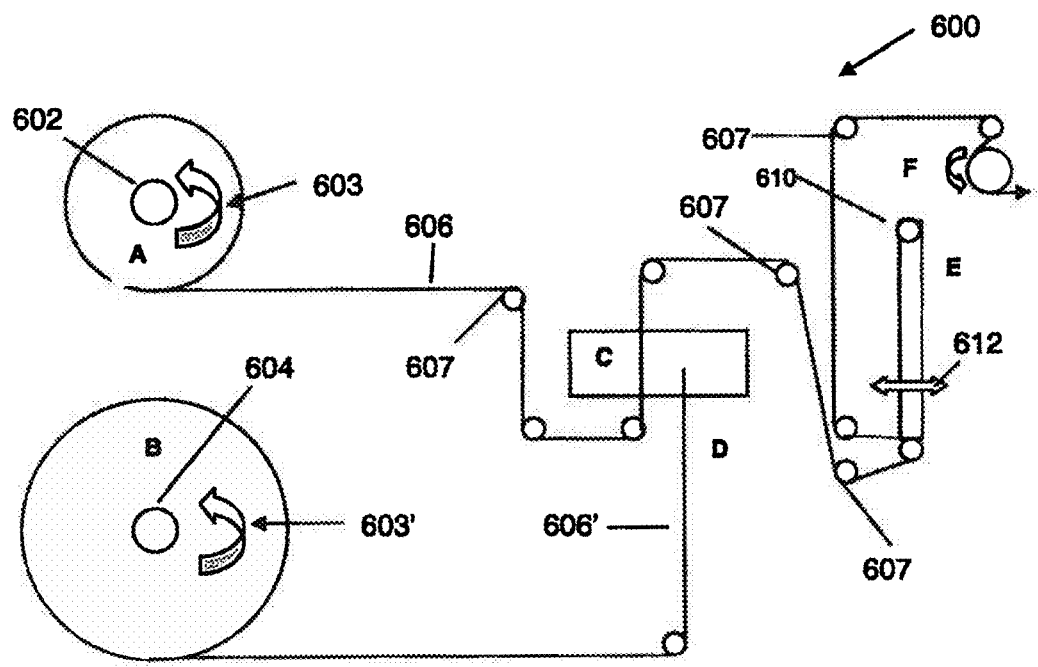
FIG. 7 is an exemplary base material feeding machine in accordance with one non-limiting embodiment.

In one embodiment, still referring to FIG. 5, a feeding system for the base material 426 can comprise the first base material feeder 438, the second base material feeder 440, the one or more optional material feeders 442, and/or various optional components 444 of the feeding system. The feeding system can be used to feed any suitable base material 426 into the production line based on what type of products or articles are being produced by or processed on the production line. An example feeding system and some optional components of the feeding system are described in further detail in FIG. 7.

Figure 6:
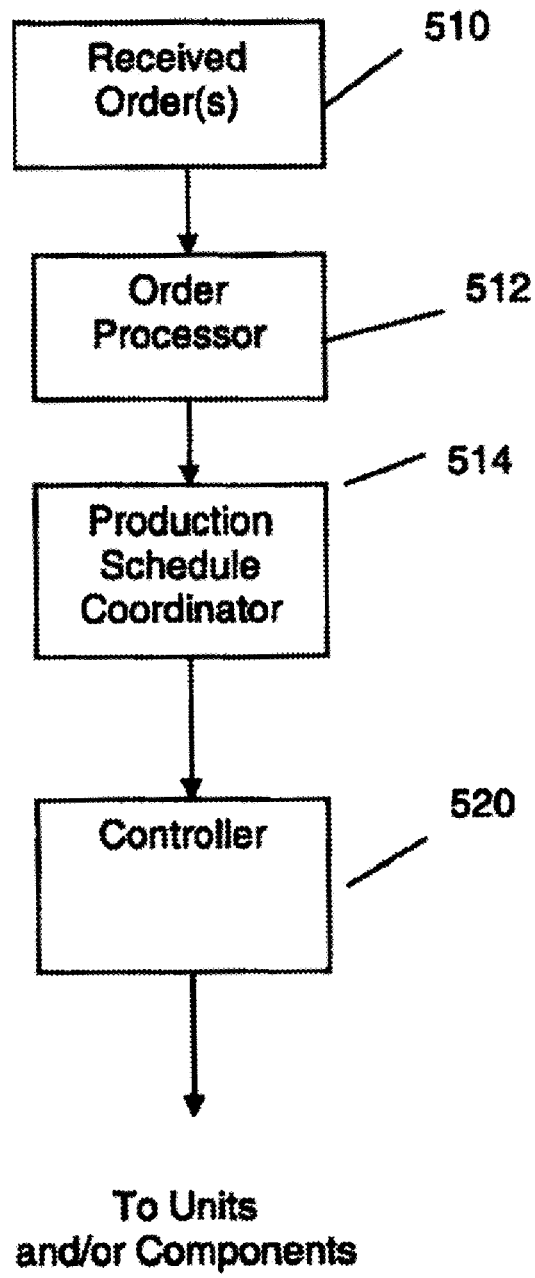
FIG. 6 is a flow chart illustrating how received order information is processed for use in the production line in accordance with one non-limiting embodiment.

In one embodiment, referring to FIG. 6, a flow chart illustrates an example of how received order information and/or received product orders are processed for use in the production line. First, received orders 510 or received order information is received from one or more customers. The "received orders" can also be financial commitments to purchase products made by the one or more customers and may not specifically be "orders". After the orders are received, they can be sent to an order processor 512 or server. In one embodiment, the order processor 512 can be a computer, a piece of software, and/or a piece of hardware, for example, which can sort, track, categorize, combine, and/or monitor, for example, the received orders 510 or the received order information. An optional, production schedule coordinator 514 can receive the processed order information from the order processor 512. In one embodiment, the production schedule coordinator 514 can be a computer, a piece of software, a piece of hardware, and/or a scheduler. The production schedule coordinator 514 can compare a proposed production schedule for the production line to the actual order information to determine if the proposed production schedule should be modified or left the same, for example. In various embodiments, the production schedule coordinator 514 can be in communication with a controller 520 or one or more controllers such that various production information can be provided to the controller 520. The controller 520 can then direct the various units to activate, inactivate, perform a first function, perform a second function, and/or perform at least a third function, for example, to accommodate a particular received customer order or more than one received customer orders.

In various embodiments, the machines of the present disclosure can be changed over from producing a first product or one or more different products to producing a second product or one or more different products by merely using software running the various units and/or running the controller. Such a software changeover can significantly decrease the time required for a changeover in a production line, as physical components of the production line do not need to be changed out. Any suitable method of running a first software module to create a first product or a first set of products on a production line to running a second software module to create a second product or a second set of products on the production line is within the scope of the present disclosure.

The ability to merely make a software changeover is a significant improvement over the related art, as the software can control the functionality of the various units based on received order information and/or received product orders in comparison to physical changeovers and estimated or projected production schedules not based on real time product orders. In one example embodiment, the software can be used to activate, inactivate, and/or change one or more of the functions performed by the various units, during a single run of a production line, based on the received order information or the received product orders. This can allow a manufacturer to make more than one different product during a single run of the production line.

Although the present disclosure addresses taking received product order information and producing various products using such information on the production line, the received product orders can also be taken out of inventory and then the system can replenish the depleted inventory on a real time basis, or at least in a much shorter time period than related production systems. In one example embodiment, if a product order is received for 100 units of a first product and 50 units of a second product, the 100 units of the first product and the 50 units of the second product can be taken out of a manufacturer's inventory. The production line can then be instructed by the controller, based on the amount of inventory depleted, to make 100 units of the first product and 50 units of the second product on a real time basis. Of course, in certain embodiments, products can be taken from inventory and made using the production line of the present disclosure to fully fill a received product order.

In one embodiment, any suitable feeding or unwinding device can be used to feed a base material or other materials into the production line. The feeding or unwinding device can be positioned in the production line as illustrated in FIG. 5, for example. The feeding or unwinding devices can represent any one of the first base material feeder 438, the second base material feeder 440, or the one or more optional material feeders 442, for example. Various components of the feeding or unwinding device can represent the optional components 444 of FIG. 5, for example. In various embodiments, the base material can be a carrier web or other material for making absorbent articles, for example. In one example embodiment, referring to FIG. 7, a base material can be fed into the production line using a feeding device 600. The feeding device 600 can comprise a roll of material "A" positioned on a first rotatable mandrel 602 and a second, stand-by roll of material "B" positioned on a second rotatable mandrel 604. The rolls of material A and B can rotate in the direction indicated by arrows 603 and 603', respectively, and/or can rotate in the opposite direction, for example, based on a particular production line requirement. The rolls of material A and B on the mandrels 602 and 604, respectively, can be any suitable carrier webs and/or other materials, for example. In one embodiment, the roll of material A can comprise a material 606 and the roll of material B can comprise a material 606'. The material 606 and/or the material 606' can travel about rollers or pulley wheels 607 through the feeding device 600. In various embodiments, the material 606 can be the same as or different than the material 606'. The feeding device 600 can also comprise a splicing box "C" that can comprise an automatic splicer and a cutting member, for example. The cutting member can be used to cut the material 606 or the material 606' depending on which roll of material (A or B) is close to being depleted or nearing its end. In an example embodiment, the material 606' can comprise an end portion "D" positioned within the splicing box C. The end portion D of the material 606' can be spliced to a portion of the material 606 where the material 606 is cut by the cutting member within the splicing box C. The feeding device 600 can also comprise a pivoting tension dancer-material accumulator "E" and a driven metering roll "F". The pivoting tension dancer-material accumulator E can provide tension to the material (606 or 606') being fed through the feeding device 600 to maintain a constant or substantially constant tension on the material 606 or 606'. The pivoting tension dancer-material accumulator E can also pivot about pivot point 610 in the direction indicated by arrow 612 to accumulate material before a splice between the roll of material A and the roll of material B. As such, the material 606 or 606' can be constantly provided to the driven metering roll F to be provided to the production line, even during a roll splice.

In operation, the material 606 can initially be fed about the various rollers 607 through the splicing box C, through the pivoting tension dancer-material accumulator E, and to the driven metering roll F. The driven metering roll F can convey or move the material 606 to the production line, such as a converting line, for example. In one embodiment, during normal operation, the speed of the roll of material A and the driven metering roll F can be correlated to the speed of the production line. As small tension variations occur in the material 606, the pivoting tension dancer-material accumulator E can pivot about the pivot point 610 and a signal based on this movement can be sent to the driven metering roll F to speed it up or slow it down to maintain a constant tension on the material 606.

Further to the above, as the material 606 of the roll of material A is nearing its end, the pivoting tension dancer-material accumulator E can swing to the right to "accumulate" a portion of the material 606 in storage such that the splice can take place while still feeding the production line with material. As the material 606 of the roll of material A nears its end, the roll of material A can stop rotating while the material 606 continues to feed to the driven metering roll F from the material accumulated by the pivoting tension dancer-material accumulator E. As the accumulated material is fed to the driven metering roll F, the pivoting tension dancer-material accumulator E can start to swing back to the left. Meanwhile, the cutting member in the splicing box C can cut the material 606 near its end and the automatic splicing device can splice the end portion D of the material 606' to an end portion of the material 606. The material 606' from the roll of material B can then start rotating about the mandrel 604 at a normal operating speed. Before the roll of material B runs out, a new roll of the material 606 is loaded onto the mandrel 602, and the above-discussed process is repeated, but now with the roll of material on the mandrel 602 being the standby roll. Of course, it will be appreciated that any other suitable feeding or unwinding devices and/or feeding systems are within the scope of the present disclosure.

In one embodiment, the present disclosure, in part, is directed to a method of producing more than one absorbent article during a single run of a production line. The method can comprise providing a plurality of units positioned along the production line where each unit is configured to perform at least one function. The method can further comprise assembling a first group of the units in series with each other, assembling a second group of the units in parallel with at least one of the units in the first group, and providing a base material to the production line. The method can further comprise activating, inactivating, and/or changing at least one function of at least one of the units in the first group and/or the second group based on a received order for absorbent articles or other products. The method can further comprise providing a first path through the production line for a first portion of the base material to produce a first absorbent article or first product and providing a second path through the production line for a second portion of the base material to produce a second absorbent article or second product. The first path through the production line can be the same as or different than the second path through the production line. The first absorbent article or first product can be different than or the same as than the second absorbent article or second product and can have the same intended use as the second absorbent article or second product or a different intended use. In one example embodiment, the first absorbent article can be a diaper and the second absorbent article can be a cleaning article. At least one of the units can be configured to perform a first function to create the first absorbent article or first product and can be configured to perform a second function to create the second absorbent article or second product during the single run of the production line.

In one embodiment, the method can further comprise packaging the first absorbent article or first product and the second absorbent article or second product together in a package. In other various embodiments, the method can further comprise packaging a plurality of absorbent article or other articles or products together in a package. In one embodiment, the method can further comprise applying a first amount of an absorbent material or other material to the first portion of the base material for formation of the first absorbent article or first product, and applying a second amount of the absorbent material or other material to a second portion of the base material for formation of the second absorbent article or second product.

It is to be appreciated that the systems and methods disclosed herein may be utilized with various different types and aspects of methods and apparatuses relating to converting lines, such as, for example, described in the U.S. patent application Ser. No. 12/544,363 , entitled "RECONFIGURABLE CONVERTING LINE FOR FABRICATING ABSORBENT ARTICLES," filed on Aug. 20, 2009; U.S. patent application Ser. No. 12/544,302, entitled "MODULAR CONVERTING LINE FOR FABRICATING ABSORBENT ARTICLES," filed on Aug. 20, 2009; U.S. patent application Ser. No. 12/544,268, entitled "SYSTEMS AND METHODS FOR CONTINUOUS DELIVERY OF WEB MATERIALS," filed on Aug. 20, 2009; and U.S. patent application Ser. No. 12/544,346, entitled "SPEED CHANGE KIT FOR AN ABSORBENT ARTICLE CONVERTING LINE," filed on Aug. 20, 2009, all of which are incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A machine for manufacturing at least two different absorbent articles during a single run of a production line, the machine comprising:
    a first unit at a first region of the production line, the first unit configured to perform a first function;
    a second unit at a second region of the production line, the second unit configured to perform a second function;
    the first unit positioned in series with the second unit;
    a third unit at a third region of the production line, the third unit configured to perform a third function;
    a fourth unit at a fourth region of the production line, the fourth unit configured to perform a fourth function;
    the fourth unit positioned in series with the second unit;
    the third unit positioned in parallel with the first unit, the second unit, or the fourth unit; and
    a controller configured to activate at least one of the first unit, the second unit, the third unit, and the fourth unit based on a received order for absorbent articles;
    wherein the machine is configured to produce a first absorbent article having a first intended use and a second absorbent article having a second intended use during the single run of the production line, and wherein the first absorbent article is different than the second absorbent article;
    wherein the first absorbent article is selected from the group consisting of: disposable diapers, adult incontinence articles, feminine hygiene products, and wipes; and
    wherein the second absorbent article is selected from the group consisting of: disposable diapers, adult incontinence articles, feminine hygiene products, and wipes.

2. The machine of claim 1, wherein at least one of the first unit, the second unit, the third unit, and the fourth unit comprises at least two units.

3. The machine of claim 1, wherein at least one of the first function, the second function, the third function, and the fourth function comprises at least two functions.

4. The machine of claim 1, wherein the first intended use of the first absorbent article is the same as the second intended use of the second absorbent article.

5. The machine of claim 1, further comprising at least a fifth unit configured to provide at least a fifth function.

6. The machine of claim 5, wherein the fifth unit is positioned in series with the fourth unit.

7. The machine of claim 5, wherein the fifth unit is positioned in series with the third unit and is positioned in parallel with the fourth unit.

8. The machine of claim 1, further comprising an absorbent material dispensing device located at one of the units, wherein the absorbent material dispensing device is configured to apply a first amount of an absorbent material to a first portion of the base material for formation of the first absorbent article, and wherein the absorbent material dispensing device is configured to apply a second amount of the absorbent material to a second portion of the base material for formation of the second absorbent article.

9. The machine of claim 1, further comprising a material removing device located at one of the units, wherein the material removing device is configured to remove a first amount of the base material from a first portion of the base material for formation of the first absorbent article, and wherein the material removing device is configured to remove a second amount of the base material from a second portion of the base material for formation of the second absorbent article.

10. The machine of claim 1, further comprising an application device located at one of the units, wherein the application device is configured to apply a first item to a first portion of the base material for formation of the first absorbent article, and wherein the application device is configured to apply a second item to a second portion of the base material for formation of the second absorbent article.

11. The machine of claim 1, further comprising a pigment application device located at one of the units, wherein the pigment application device is configured to apply a first amount of a pigment to the first absorbent article in a first pattern, and wherein the pigment application device is configured to apply a second amount of the pigment to the second absorbent article in a second pattern.

12. The machine of claim 1, wherein at least the second unit is configured to be removed from the production line, the machine further comprising a fifth unit configured to perform a fifth function, wherein the fifth unit is configured to replace the second unit in the production line.

13. A converting line for producing different absorbent articles during a single run of the converting line, the converting line comprising:
    a first unit at a first region of the converting line, the first unit configured to perform at least a first function;
    a second unit at a second region of the converting line, the second unit configured to perform at least a second function;
    the first unit positioned in series with the second unit;
    a third unit at a third region of the converting line, the third unit configured to perform at least a third function;
    a fourth unit at a fourth region of the converting line, the fourth unit configured to perform at least a fourth function;
    the third unit positioned in parallel with the first unit, the second unit, or the fourth unit; and
    a controller configured to activate at least one of the first unit, the second unit, the third unit, and the fourth unit based on one or more received orders for absorbent articles;
        wherein the converting line is configured to produce a first absorbent article and a second absorbent article during the single run of the converting line, and wherein the first absorbent article is different than the second absorbent article;
    wherein the first absorbent article is selected from the group consisting of: disposable diapers, adult incontinence articles, feminine hygiene products, and wipes; and
    wherein the second absorbent article is selected from the group consisting of: disposable diapers, adult incontinence articles, feminine hygiene products, and wipes.

14. A method of producing more than one absorbent article during a single run of a production line, the method comprising:
    providing a plurality of units positioned along the production line, each unit configured to perform at least one function;
    assembling a first group of the units in series;

assembling a second group of the units in parallel with the first group of the units;

providing a base material to the production line;

activating at least one function of at least one of the units in the first group or the second group based on a received order for absorbent articles;

inactivating at least one function of at least one of the units in the first group or the second group based on the received order for absorbent articles;

providing a first path through the production line for a first portion of the base material to produce a first absorbent article; and providing a second path through the production line for a second portion of the base material to produce a second absorbent article, wherein the first absorbent article is different than the second absorbent article, and wherein the first absorbent article is selected from the group consisting of: disposable diapers, adult incontinence articles, feminine hygiene products, and wipes; and wherein the second absorbent article is selected from the group consisting of: disposable diapers, adult incontinence articles, feminine hygiene products, and wipes.

15. The method of claim 14, wherein the first path through the production line is the same as the second path through the production line.

16. The method of claim 14, wherein the first absorbent article has the same intended use as the second absorbent article.

17. The method of claim 14, further comprising packaging the first absorbent article and the second absorbent article together in a package.

18. The method of claim 14, wherein at least one of the plurality of units is configured to perform a first function to create the first absorbent article and is configured to perform a second function to create the second absorbent article during the single run of the production line.

19. The method of claim 14, further comprising:

applying a first amount of an absorbent material to the first portion of the base material for formation of the first absorbent article; and applying a second amount of the absorbent material to a second portion of the base material for formation of the second absorbent article.

20. The method of claim 14, wherein the first absorbent article is a diaper, and wherein the second absorbent article is a wipe.

* * * * *